United States Patent
Brüggemann et al.

(10) Patent No.: US 9,439,405 B2
(45) Date of Patent: *Sep. 13, 2016

(54) MOUSE λ LIGHT CHAIN LOCUS

(71) Applicant: CRESCENDO BIOLOGICS LIMITED, Cambridge (GB)

(72) Inventors: Marianne Brüggemann, Cambridge (GB); Xiangang Zou, Cambridge (GB)

(73) Assignee: Crescendo Biologics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/654,007

(22) Filed: Oct. 17, 2012

(65) Prior Publication Data

US 2013/0046079 A1    Feb. 21, 2013

Related U.S. Application Data

(63) Continuation of application No. 12/476,087, filed on Jun. 1, 2009, now Pat. No. 8,367,888, which is a continuation of application No. 10/481,395, filed as application No. PCT/GB02/02867 on Jun. 21, 2002, now Pat. No. 7,541,513.

(30) Foreign Application Priority Data

Jun. 21, 2001   (GB) .................................. 0115256.0

(51) Int. Cl.
| A01K 67/00 | (2006.01) |
| A01K 67/027 | (2006.01) |
| C07K 16/00 | (2006.01) |

(52) U.S. Cl.
CPC ........... *A01K 67/0276* (2013.01); *C07K 16/00* (2013.01); *A01K 2217/075* (2013.01); *A01K 2227/105* (2013.01); *C12N 2800/30* (2013.01)

(58) Field of Classification Search
CPC ................. A01K 67/0278; A01K 2227/105; A01K 2267/01; A01K 2207/15; A01K 2217/05; A01K 2217/075; C07K 16/00; C07K 2317/22; C07K 2317/569
USPC .................................................... 800/18, 13
See application file for complete search history.

(56) References Cited

U.S. PATENT DOCUMENTS

| 5,770,429 A | 6/1998 | Lonberg et al. | |
| 6,162,963 A | 12/2000 | Kucherlapati et al. | |
| 7,541,513 B2 * | 6/2009 | Bruggeman et al. | 800/22 |
| 8,367,888 B2 * | 2/2013 | Bruggemann et al. | 800/18 |

FOREIGN PATENT DOCUMENTS

| EP | 1399559 | 4/2008 |
| WO | WO 90/04036 | 4/1990 |
| WO | WO94/02602 | 2/1994 |
| WO | WO96/33735 | 10/1996 |
| WO | WO 98/24884 | * 6/1998 |
| WO | WO98/24884 | 6/1998 |
| WO | WO00/26373 | 5/2000 |
| WO | WO 02/12437 A2 | 2/2002 |
| WO | WO 02/066630 | 8/2002 |
| WO | WO 02/085944 A2 | 10/2002 |
| WO | WO 02/085945 | * 10/2002 |
| WO | WO 03/002609 A2 | 1/2003 |
| WO | WO 2004/049794 A2 | 6/2004 |

OTHER PUBLICATIONS

Corcos et al. (1995) Current Biology, vol. 5, 1140-1148.*
Butler (1998) Revue Scientifique et Technique Office International Des Epizooties. vol. 17, No. 1, pp. 43-70.*
Houdebine et al. (2000) Transgenic Research vol. 9, 305-320.*
Kolb et al. (1999) Gene, vol. 227, pp. 21-31.*
Sigmund, C., (2000) Arterioscler. Thromb. Vasc. Biol., vol. 20, 1425-1429.*
Araki et al., Biochem (Tokyo) 122: 977-982 (1997).
Bedell et al., Genes & Development 11: 1-10 (1997).
Bell et al., The EMBO Journal 13(4): 816-826 (1994).
Blomberg et al., Proc Natl Acad Sci 78(6): 3765-3769 (1982).
Bossy et al., International Immunology. 3(11): 1081-1090 (1991).
Boudinot et al., European Journal of Immunology 24(9): 2013-2017 (1994) (Abstract XP-002238056).
Brüggemann etal., Proc. Natl. Acad. Sci. USA 86: 6709-6713 (1989).
Brüggemann, Archivum Immunologiae et Therapiae, Experimentalis, 49: 203-208 (2001).
Butler, Revue Scientifique at Technique Office International Des Epizooties 17(1): 43-70 (1998).
Carson et al., Immunogenetics 29: 173-179 (1989).
Chen et al. The EMBO Journal 12(3): 821-830 (1993).
Chen et al., Int Immunol, 5(6): 647-656 (1993).
Cheng et al., Nature 378: 303-306 (1995).
Deng et al., Molecular and Cellular Biology 12(8): 3365-3371 (1992).
DiSanto et al., Proc. Natl. Acad. Sci. USA 92: 377-381 (1995).
Donohoe et al., The Journal of Immunology 164: 5269-5276 (2000).
Dunnick et al., JEM, pp. 1-11 (2009).
Ehlich et al., Cell 72: 695-704 (1993).
Eisen et al., Ann Rev Immunol 3: 337-365 (1985).
Fruman et al., Science 283: 393-397 (1999).
Glaser et al., Nature Genetics 37(11): 1187-1193 (2005).
Goldstein, Nature Medicine 7(10): 1079-1080 (2001).

(Continued)

*Primary Examiner* — Anne Marie S Wehbe
(74) *Attorney, Agent, or Firm* — Wolf, Greenfield & Sacks, P.C.

(57) ABSTRACT

The present invention provides in a first aspect a mouse in which the λ (lambda) light chain locus has been functionally silenced. In one embodiment, the mouse λ light chain locus was functional silenced by deletion of acne segments coding for the λ light chain locus. In a further aspect, a mouse containing functionally silenced λ and κ (kappa) L chain loci was produced. The invention is useful for the production of antibodies, for example heterologous antibodies, including heavy chain only antibodies.

8 Claims, 6 Drawing Sheets

(56) References Cited

OTHER PUBLICATIONS

Gollahon et al., Immunol 141: 2771-2780 (1988).
Gong et al., Science 272: 411-414 (1996).
Gu et al., Cell 73: 1155-1164 (1993).
Hamers-Casterman et al., Nature 363(6428): 446-448 (1993) (Abstract XP-002238053).
Hasty et al., Molecular and Cellular Biology 11(11): 5586-5591 (1991).
He et al., Endocrinology 142(5): 2070-2077 (2001).
Hogan et al., In: Manipulating the Mouse Embryo, Section E, a laboratory manual, Cold Spring Harbor Laboratoy Press, Cold Spring Harbor, pp. 217-251 (1994).
Hogan et al., In: Manipulating the Mouse Embryo. Section F, a laboratory manual, Cold Spring Harbor Laboraty Press, Cold Spring Harbor, pp. 253-289 (1994).
Houdebine et al., Transgenic Research 9: 305-320 (2000).
Hunt et al., Journal of Immunological Methods 65: 199-205 (1983).
Jiang et al., Current Biology 7: R321-R323 (1997).
Joyner, Gene Targeting: A Practical Approach, Oxford University Press, second edition—cover 1 and Table of contents (2000).
Kitamura et al., Nature 350: 423-426 (1991).
Kitamura et al., Cell 69: 823-831 (1992).
Kolb et al., Gene 227: 21-31 (1999).
Kuhn et al., Current Opinion in Immunology 9: 183-188 (1997).
Lariviere et al., J. Pharm. and Exp. Therap. 297: 467-473.
Leiter et al., Diabetologia 45: 296-308 (2002).
LePage et al., PNAS 97(19); 10471-10476 (2000).
Li et al., Proc. Natl. Acad. Sci. 93: 6158-6162 (1996).
Liu et al., Genetics 150: 1155-1168 (1998).
Lonberg, Nature Biotechnology 23(9): 1117-1125 (2005).
Madsen et al., Proc. Natl. Acad. Sci. USA 96: 10338-10343 (1999).
Manis et al., J. Exp. Med. 188(8): 1421-1431 (1998).
March et al., Analytical Biochemistry 60: 149-152 (1974).
Miller et al., Proc. Natl. Acad. Sci. USA 78(6) 3829-3633 (1981).
Miller et al., The Journal of Immunology 141(7): 2497-2502 (1988).
Miller et al., Nature 295: 428-430 (1982).
Mombaerts et al., Cell 68: 869-877 (1992).
Motoyama et al., PNAS 88: 7933-7937 (1991).
Müller, Mechanisms of Development 82(1-2): 3-21 (1999).
Nagy, Genetics 26: 99-109 (2000).
Nicholson et al., The Journal of Immunology 163: 6898-6906 (1999).
Nishimoto et al., Proc. Natl. Acad. Sci. USA 88: 6284-6288 (1991).
Osoegawa et al., Genome Research 10: 116-128 (2000).
Pettitt et al., Nature Methods 6(7): 493-496 (20009).
Popov et al., J. Exp. Med. 189(10): 1611-1619 (1999).
Ramirez-Solis et al., Nature 378: 720-724 (1995).
Reilly et al., Proc Natl Acad Sci 81: 2484-2488 (1984).
Ren et al., Genomics 84: 668-695 (2004).
Riechmann et al., Journal of Immunological Methods 231(1-2): 25-38 (1999) (Abstract XP-002238054).
Sage et al., Genes & Development 14: 3037-3050 (2000).
Sanchez et al., Inter. Rev. Immunol. 13: 357-368 (1996).
Sauer et al., Nucleic Acids Research 17(1): 147-161 (1989).
Sauer, Methods: A Companion to Methods in Enzymology 14: 381-392 (1998) (Article No. ME980593).
Sauer et al., Proc Nati Acad Sci 85: 5166-5170 (1988).
Sauer et al., The New Biologise, 2(5): 441-449 (1990).
Schiff et al., Intern. Rev. Immuol. vol. 8: 135-145 (1992).
Schlake et al., Oncogene 18: 6078-6082 (1999).
Selfridge et al., Somatic Cell and Molecular Genetics 18(4): 325-336 (1992).
Selsing et al., Proc Natl Acad Sci USA 79: 4681-4685 (1982).
Seung et al., Trends in Genetics 20(2): 59-62 (2004).
Shinkai et al., Cell 68: 855-867(1992).
Sigmund, Arterioscler. Throm. Vasc. Biol., p. 1425-1429.
Smith et al., Nature Genetics 9: 376-385 (1995).
Stacey et al., Mol. Cell, Biol., 14(2): 1009-1016 (1994).
Storb et al., Mol. Cell Biol. 9(2): 711-718 (1989).
Stricklett et al., Am J Physiol Renal Physiol 276: 651-657 (1999).
Sun et al., J. Exp. Med. 193(6): 699-711 (2001).
Sutherland et al., . Genomics 52: 37-43 (1998).
Te Riele et al., Proc Natl. Acad. Sci. USA 89: 5128-5132 (1992).
Thompson et al., Journal of Neuroimmunology 2: 321-330 (1982).
Torres et al., Laboratory Protocols for Conditional Gene Targeting, Oxford University Press: cover, table of contents and pp. 23 to 25, 70 and 71 (1997).
Transue et al., Proteins 32(4): 515-522 (1998) (Abstract XP-002238055).
Turner et al., Nature 378: 298-302 (1995).
van Deursen et al., Proc. Natl. Acad. Sci. USA 92: 7376-7380 (1995).
Vasquez et al., PNAS 98(15): 8403-8410 (2001).
Vooijs et al., EMBO Reports 2(4): 292-97 (2001).
Weiss et al., The EMBO Journal 6(4): 927-932 (1987).
Weiss et al., Eur. J. Immunol. 15: 765-768 (1985).
Whyatt et al., Nucleic Acids Res. 25(12): 2381-2388 (1997).
Wu et al., Nature Protocols 3(6): 1056-1076 (2008).
Yeung et al., Current Opinion in Immunology 6: 298-307 (1994).
Zheng et al., Molecular and Cellular Biology 20(2): 648-655 (2000).
Zou et al., Eur. J. Immunol. 25: 2154-2162 (1995).
Zou et al., The Journal of Immunology 170: 1354-1361 (2003).
Zou et al., J. Immunology 175: 3769-3779 (2005).
Zou et al., The FASEB Journal 10: 1227-1232 (1996).
Zou et al., EMBO 3 12(3): 811-820 (1993).
Notice of Opposition to a European Patent—Harbour Antibodies B.V. (Jan. 28, 2009).
Notice of Opposition to a Euroean Patent—John Gerard Leeming (Jan. 29, 2009).
Notice of Opposition to a European Patent—Merus B.V (Jan. 30, 2009).
Priority Document (GB0115256.0) (Jun. 21, 2001).
International Preliminary Examination Report (PCT/GB02/02867) (Dec. 2, 2003).
Declaration Declaration by Professor Peterson.
Declaration by Professor Montoliu.
Declaration by Vivek Iyet.
Declaration of Dr. Simon Andrews (Mar. 2, 2011).
Declaration by Dr. Anton Berns (Mar. 3, 2011).
Declaration of Ton Logtenberg (Mar. 3, 2011).
Statement by Dr. Andrei Popov (Dec. 2, 2009).
Alexander et al., Proc. Natl. Acad. Sci. USA 79: 3260-3264 (1982).
Hamers-Casterman et al., Nature 363: 446-448 (1993).
Matheson et al., International Immunology 21(8): 957-966 (2009).
Utsumi et al., The Subunits of Purified Rabbit Anitibody 3(9): 1329-1338 (1964).
Young et al., Transgenic Res 20: 1139, Abstract 59 (2011).
Zou et al. JEM 204(13): 3271-3283 (2007).
Board of Appeal Decision in appeal T1526/11-3.3.08 of decision of Opposition Division in EP 1399559 (EP 02732970.5), Mar. 17, 2015. 22 pages.
EPO communication pursuant to Rule 82(2) in connection with EP 02732970.5, dated Apr. 28, 2015. 18 pages.
Opposition Division Decision in connection with EP 02732970.5, dated May 10, 2011. 22 pages.
Opposition by Crescendo Biologics Limited to European Patent No. EP 1776383. 46 pages.
Declaration and Curriculum Vitae of Andrei V. Popov, Ph.D. filed in EP 02732970.5, dated Feb. 3, 2011. 7 pages.
Declaration and Curriculum Vitae of Anne E. Corcoran, Ph.D. filed in opposition against EP 1776383, dated May 15, 2015. 13 pages.
Declaration and Curriculum Vitae of Daniel Corcos, MD, Ph.D. filed in opposition against EP 1776383, dated May 20, 2015. 18 pages.
Declaration and Curriculum Vitae of Lutz Riechmann, Ph.D. filed in opposition against EP 1776383, dated May 20, 2015. 40 pages.
Declaration and Curriculum Vitae of Michael R. Clark, Ph.D. filed in opposition against EP 1776383, dated May 18, 2015. 30 pages.
Declaration and Curriculum Vitae of Xiangang Zou, Ph.D. filed in EP 02732970.5, dated Feb. 3, 2011. 6 pages.
Declaration of Marianne Bruggemann, Ph.D. submitted in U.S. Appl. No. 10/481,395, dated Mar. 6, 2007. 3 pages.

(56) References Cited

OTHER PUBLICATIONS

Declaration of Rudi W. Hendriks, Ph.D. filed in EP 02732970.5, dated Nov. 22, 2010. 6 pages.
[No Author Listed] Report submitted by Opponent 3 filed in EP 02732970.5 on Dec. 2, 2010 entitled "Description of MuVλ-KO project P07078-R14" 6 pages.
Arbabi Ghahroudi et al., Selection and identification of single domain antibody fragments from camel heavy-chain antibodies. FEBS Lett. Sep. 15, 1997;414(3):521-6.
Barthelemy et al., Comprehensive analysis of the factors contributing to the stability and solubility of autonomous human VH domains. J Biol Chem. Feb. 8, 2008;283(6):3639-54. Epub Nov. 28, 2007.
Boder et al., Yeast surface display for screening combinatorial polypeptide libraries. Nat Biotechnol. Jun. 1997;15(6):553-7.
Bond et al., A structure-based database of antibody variable domain diversity. J Mol Biol. May 6, 2005;348(3):699-709.
Cai et al., A melanoma-specific VH antibody cloned from a fusion phage library of a vaccinated melanoma patient. Proc Natl Acad Sci U S A. Jun. 25, 1996;93(13):6280-5.
Cai et al., Comparison of fusion phage libraries displaying VH or single-chain Fv antibody fragments derived from the antibody repertoire of a vaccinated melanoma patient as a source of melanoma-specific targeting molecules. Proc Natl Acad Sci U S A. Aug. 19, 1997;94(17):9261-6.
Collins et al., A mouse for all reasons. A mouse for all reasons.
Davies et al., 'Camelising' human antibody fragments: NMR studies on VH domains. FEBS Lett. Feb. 21, 1994;339(3):285-90.
Davies et al., Antibody VH domains as small recognition units. Biotechnol May 1995;13(5):475-9.
Davies et al., Single antibody domains as small recognition units: design and in vitro antigen selection of camelized, human VH domains with improved protein stability. Protein Eng. Jun. 1996;9(6): 531-7.
Decanniere et al., A single-domain antibody fragment in complex with RNase A: non-canonical loop structures and nanomolar affinity using two CDR loops. Structure 1993. Apr. 15, 1999;7(4):361-70.
Deng et al., Location of Crossovers during Gene Targeting with Insertion and Replacement Vectors. Mol Cell Biol 1993 13(4):2134-40.
Desmyter et al., Crystal structure of a camel single-domain VH antibody fragment in complex with lysozyme. Nat Struct Biol. Sep. 1996;3(9):803-11.
Echelard, Year of the ox. Nat Biotechnol. Feb. 2009;27(2):146-7.
Galler et al., Surface mu heavy chain signals down-regulation of the V(D)J-recombinase machinery in the absence of surrogate light chain components. J Exp Med. Jun. 7, 2004;199(11):1523-32.
Green Antibody engineering via genetic engineering of the mouse: XenoMouse strains are a vehicle for the facile generation of therapeutic human monoclonal antibodies. J Immunol Methods. Dec. 10, 1999;231(1-2):11-23.
Green et al., Antigen-specific human monoclonal antibodies from mice engineered with human Ig heavy chain and light chain YACs. Nat Genet. May 1994;7(1):13-21.
Harmsen et al., Llama heavy-chain V regions consist of at least four distinct subfamilies revealing novel sequence features. Mol Immunol. Aug. 2000;37(10):579-90.
Hasan et al., Incomplete block of B cell development and immunoglobulin production in mice carrying the muMT mutation on the BALB/c background. Eur J Immunol. Dec. 2002;32(12):3463-71.
Hendershot et al., Assembly and secretion of heavy chains that do not associate posttranslationally with immunoglobulin heavy chain binding protein. J. Cell. Biol. 104: 761-767, 1987.
Holt et al., Domain antibodies: proteins for therapy. Trends Biotechnol. Nov. 2003;21(11):484-90.
Janssens et al., Generation of heavy-chain-only antibodies in mice. Proc Natl Acad Sci U S A. Oct. 10, 2003;103(41):15130-5.
Kellermann et al., Antibody discovery: the use of transgenic mice to generate human monoclonal antibodies for therapeutics. Curr Opin Biotechnol. Dec. 2002;13(6):593-7.
Kitamura et al., Targeted disruption of mu chain membrane exon causes loss of heavy-chain allelic exclusion. Nature. Mar. 12, 1992;356(6365):154-6.
Kuroiwa et al., Cloned transchromosomic calves producing human immunoglobulin. Nat Biotechnol. Sep. 2002;20(9):889-94.
Lonberg et al. Antigen-specific human antibodies from mice comprising four distinct genetic modifications. Nature 368, 856-859, 1994.
Lonberg Human antibodies from transgenic animals. Nat Biotechnol. Sep. 2005;23(9):1117-25.
MacPherson et al., BLySsful interactions between DCs and B cells. Nat Immunol. Sep. 2002;3(9):798-800.
MacPherson et al., IgA production without mu or delta chain expression in developing B cells. Nat Immunol. Jul. 2001;2(7):625-31.
Muyldermans et al., Unique single-domain antigen binding fragments derived from naturally occurring camel heavy-chain antibodies. J Mol Recognit. Apr. 1999;12(2):131-40.
Muyldermans Single domain camel antibodies: current status. J Biotechnol. Jun. 2001;74(4):277-302.
Orinska et al., Novel B cell population producing functional IgG in the absence of membrane IgM expression. Eur J Immunol December;32(12):3472-80. 2002.
Reiter et al., An antibody single-domain phage display library of a native heavy chain variable region: isolation of functional single-domain VH molecules with a unique interface. J Mol Biol. Jul. 16, 1999;290(3):685-98.
Tanaka et al., Single domain intracellular antibodies: a minimal fragment for direct in vivo selection of antigen-specific intrabodies. J Mol Biol. Aug. 29, 2003;331(5):1109-20.
Tanha et al., Optimal design features of camelized human single-domain antibody libraries. J Biol Chem. Jul. 6, 2001;276(27):24774-80.
Tanha et al., Selection by phage display of llama conventional V(H) fragments with heavy chain antibody V(H)H properties. J Immunol Methods. May 1, 2002;263(1-2):97-109.
Van Spriel et al., Immunotherapeutic perspective for bispecific antibodies. Immunol Today. Aug. 2000;21(8):391-7.
Vu et al., Comparison of llama VH sequences from conventional and heavy chain antibodies. Mol Immunol. Dec. 1997;34(16-17):1121-31.
Ward et al., Binding activities of a repertoire of single immunoglobulin variable domains secreted from *Escherichia coli*. Nature. Oct. 12, 1989;341(6242):544-6.
Wu et al., Length distribution of CDRH3 in antibodies. Proteins. May 1993;16(1):1-7.
Nakamura et al., Panning of a phage VH library using nitrocellulose membranes: application to selection of a human VH library. J Biochem. Feb. 2001;129(2):209-12.
Tanha et al., Optimal design features of camelized human single-domain antibody libraries. J Biol Chem. Jul. 6, 2001;276(27):24774-80. Epub May 2, 2001.

\* cited by examiner

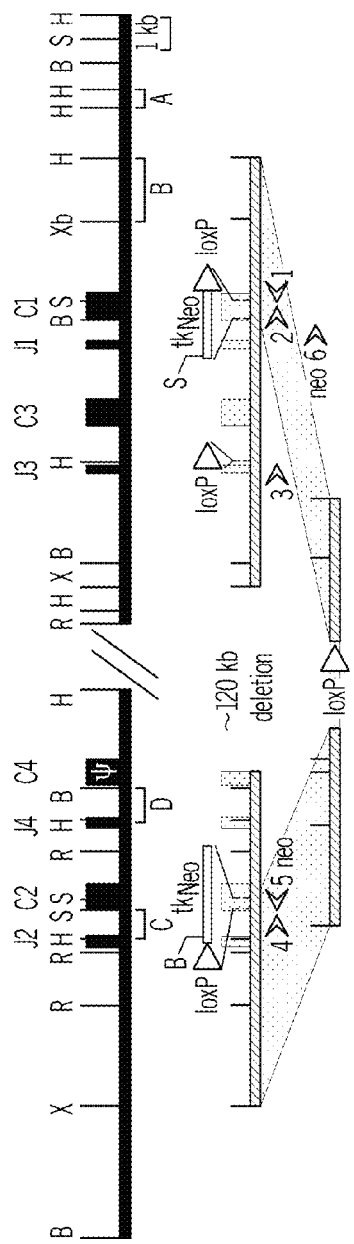 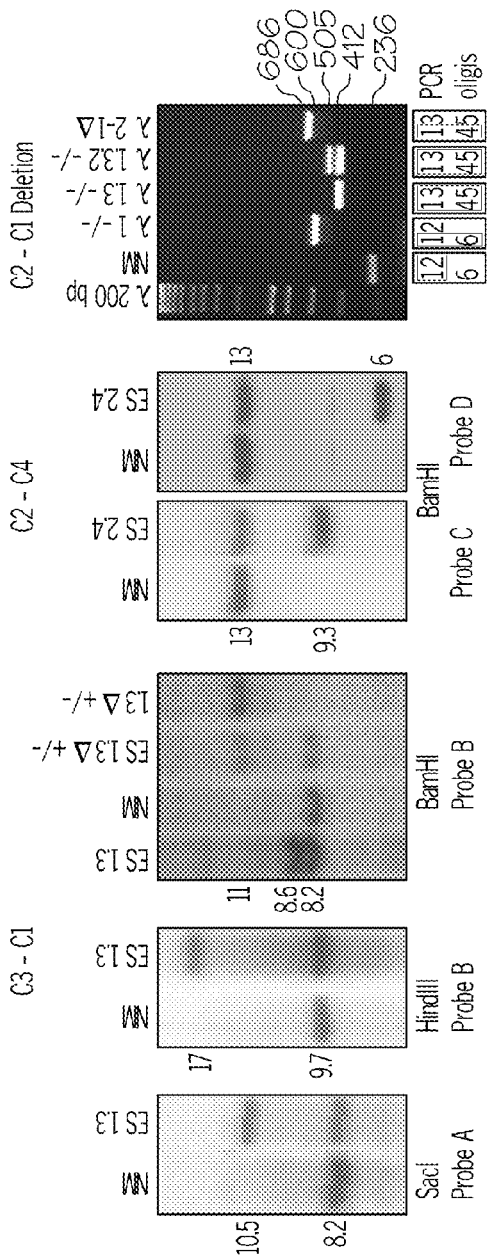
FIG. 1A
FIG. 1B

MOUSE λ LIGHT CHAIN LOCUS

This application is a continuation of U.S. application Ser. No. 12/476,087 filed Jun. 1, 2009 (allowed), which is a continuation of U.S. application Ser. No. 10/481,395 filed Feb. 10, 2004, now U.S. Pat. No. 7,541,513, which is a 371 of PCT/GB02/02867 filed Jun. 21, 2002. The entire contents of the above-identified applications are hereby incorporated by reference.

This application contains a sequence listing submitted electronically via EFS-web, which serves as both the paper copy and the computer readable form (CRF) and consists of a file entitled "13-654007 seqlist.txt", which was created on Oct. 18, 2012, which is 4,096 bytes in size, and which is herein incorporated by reference in its entirety.

The present invention relates to mice in which the λ (lambda) light (L) chain locus and/or the λ and κ (kappa) L chain loci have been functionally silenced, and to antibodies produced by such mice.

B-cells express surface immunoglobulin (Ig) either with κ (kappa) or λ L chain, a choice which is termed isotype exclusion. The proportion of antibodies containing a κ or λ L chain varies considerably in the different species but in the mouse only a few percent of antibodies express λ. L chain genes are encoded by 2 different loci, the κ or λ L chain loci, and in the mouse there is an extensive number of V(variable)κ genes upstream of 5 J(joining)κ and 1 C(constant region)κ gene. Although the κ locus is over 10-times larger than the λ locus, with more then 100 V genes, this extensive complexity is not regarded as a reason that most mouse antibodies carry a κ L chain. It may be that the mouse κ locus is simply more efficient in DNA rearrangement which is supported by the finding that in the majority of cells with rearranged Vκ the λ locus is still in germline configuration whilst in most cells expressing λ L chain the κ locus is either non-productively rearranged or deleted.

Several mouse strains with silenced κ L chain locus have been described. They were generated by homologous integration of a selectable marker gene in Cκ or targeted removal of Cκ or Jκ (see for example Zou, X. et al., 1995, Eur. J. Immunol 25(8): 2154-2162). Silencing expression of κ L chain shed light on isotype exclusion and L chain activation and it was concluded that κ and λ expression are separate and independent events. Although homozygous $\kappa^{-/-}$ mice compensate for the κ deficiency with increased λ production their splenic B-cells and $\mu^+$ cells in the bone marrow can be reduced compared to normal mice. This may suggest that λ L chain rearrangement and expression is perhaps a less efficient process. However, despite the lack of κ L chain these mice are healthy and can mount an efficient immune response.

During B-cell development gene segments encoding Ig H chains rearrange first by D to JH recombination at the pro B-cell stage. This is followed by VH to D-JH recombination at the pre B-I stage and if a μ H chain can pair with a surrogate L chain, consisting of $V_{preB}$ and λ5 protein, this forms a surfaced expressed pre B-cell receptor (pre BCR) at the B-II differentiation stage. Cell surface expression of the pre BCR induces proliferation and after several divisions large pre B-II cells differentiate into small resting pre B-II cells. The pre B-II stage with a defined ratio of large and small pre B cells has been identified by surface expression of the IL-2 receptor α chain, CD25. At the transition from pre B-II to immature B cell L chain V-J rearrangement occurs where the surrogate L chain is replaced by κ or λ. At this stage the cells can leave the bone marrow for further differentiation into plasma cells or memory cells in secondary lymphoid organs such as spleen or lymph nodes.

B-cell development without L chain has not been fully elucidated in the prior art. The BCR consists of two Ig H chains each associated with one Ig L chain in conjunction with the Igα/Igβ coreceptor. These six chains must assemble correctly in the endoplasmic reticulum (ER) to allow transport and cell surface expression of IgM to progress B-cell development. Immature B-cells without L chain are not maintained and a lack of surface IgH, Igα or Igβ expression leads to reduced signal transducer activity which can arrest B-cell maturation. H chain, synthesised prior to L chain, is chaperoned and retained in the cytoplasm but if L chain association fails single H chains, unlike L chains, undergo rapid intracellular degradation as a result of inefficient transported from the ER to the Golgi.

The mouse lambda (δ) light chain locus is about 200 kb in size and comprises 3 variable (V) region genes and 4 joining (J) segments upstream of 4 constant (C) region genes, V2-Vx-J2-C2-J4-C4-V1-J3-C3-J1-C1 (FIG. 1a). Silencing of the δ locus is difficult because homologous integration to delete or disable a single or even two Cδ genes would not be sufficient to prohibit δ light chain rearrangement and expression. To achieve this one would have to disable 2 regions: C2 and C3-C1 which are over 100 kb apart. C4 is regarded a non-functional as no protein has been found. This means two targeting constructs have to be assembled and homologously integrated in the same allele. An advantage would be the use of integrated loxP sites to allow Cre mediated deletion of the whole locus or deletion of relevant functional genes.

There is therefore the need to produce mice in which the δ light chain locus is deleted. It would also be desirable to produce mice lacking functional light chains for the production of heavy chain only antibodies—the exploitation of human antibody-producing mice, for example, is hampered by the problem that mouse lambda L chain associate with a large proportion of the expressed human Ig (or H chain).

According to a first aspect of the present invention, there is provided a mouse in which the λ light chain locus is functionally silenced. A transgenic mouse according to the invention has been produced for the first time by the present inventors. Uses of such a mouse are described below.

The λ light chain locus may be deleted in part or completely. Alternatively, the λ light chain locus may be functionally silenced through deletion of gene segments encoding for the λ light chain locus.

The exemplified procedure of rendering the mouse lambda light chain locus non-functional used two strategies of silencing all constant region genes: 1. integration of a selectable marker gene to disable individual constant region genes and 2. gene and locus deletion. As described further in the Experimental section below, this produced two lambda KO strains, $\lambda 1.3.2^{-/-}\kappa^{-/-}$ and $\lambda 1-2\Delta^{-/-}\kappa^{-/-}$ mice, with essentially the same features of a silent lambda locus. Silencing of the mouse lambda light chains verified gene/ locus organisation and showed that no additional L chain-like genes participate in B-cell development.

In a further embodiment of the invention, the κ light chain locus of the mouse may be functionally silenced. Mice with complete L chain knock-out (KO), i.e. kappa and lambda locus silenced by gene targeting, showed a block in B-cell development at the stage when L chain expression should have been completed. These mice still produce or express μ H chain. Indeed it is expected that they produce a heavy chain antibody repertoire. There is extensive commercial interest in such mice because 1) they are the first mouse strain with silenced lambda locus and 2) by crossing with existing strains they would allow to produce mice that do not express any form of mouse H or L chain.

In a further embodiment of the invention, the heavy chain locus of the mouse may be silenced by a method of gene targeting (knock-out).

The λ, κ and heavy chain loci of the mouse may be been knocked out or silenced.

In yet a further embodiment, the mouse may carry at least one transgene which comprises one or more heavy genes or loci and/or a light chain genes or loci from a heterologous species. The mouse may produce heavy chain only antibodies of the heterologous species. The heterologous species may be human.

In a further aspect of the invention, there is provided the use of a mouse as defined above to produce antibodies. The antibodies may be produced through immunisation procedures. In a preferred embodiment, the antibodies are human.

Also provided according to the present invention is a heavy chain only antibody produced in a mouse. The antibody may have heavy chains that are either single or polymerised (dimer, trimer, etc.).

Yet further provided is an antibody produced from mice as defined above.

The antibody of the invention may be monoclonal. The antibody may be human.

In another aspect of the invention, there is provided a library of VH (variable heavy chain) domains obtained from DNA of lymphocytes from one or more mice as defined above.

Also provided is a method of producing a mouse in which the λ light chain locus is functionally silenced, comprising the step of deleting at least the constant region genes C1, C2 and C3 of the λ light chain locus. The C2-C4 loci and C3-C1 loci may be deleted simultaneously or sequentially. In one embodiment, the targeting constructs shown in FIG. 1 and described below are used.

In a further aspect of the invention there is provided one or more targeting constructs for producing a mouse in which the λ light chain locus is functionally silenced. The targeting construct(s) may be as shown in FIG. 1 and/or substantially as described below with reference to FIG. 1.

Also provided according to the invention is a mouse in which the λ light chain locus is functionally silenced, with a deletion of a λ light chain gene or genes selected from the following part of the λ locus region:
(a) C3-C1;
(b) C2;
(c) C2-C1 (i.e., C2-C4-C3-C1).

The invention will be further described in the Experimental section below with reference to the accompanying figures, of which:

FIG. 1 Shows targeted integration and deletion of the mouse λ L chain locus. a, The locus is ~200 kb with 2 sets of J-C genes (J2-C2 . . . J4-C4 and J3-C3-J1-C1) separated ~110 kb. Two V genes, V2 and Vx, are located ~75 kb and ~56 kb upstream of C2, respectively, and V1 is located ~20 kb upsteam of C3. Targeted integration of C3-C1 inserts $^{tk}$Neo-laxP into C1 and loxP 3' of J3, this allows deletion of C3, J1 and 5'C1. The C2-C4 targeting construct inserts loxP-$^{tk}$Neo into C2. Both targeting constructs disable all functional C genes. Upon Cre mediated deletion the region between C2 and C1 is removed. b, Analysis of targeted integration and Cre-mediated deletion. Southern blot of normal mouse DNA (NM), ES cell DNA from clones with homologous integration in C3-C1 (ES3.1) and C2-C4 (ES2.4), and deletion of C3-C1 (ES3.1 $\Delta^{+/-}$ and 3.1 $\Delta^{-/-}$) with digests and probes (A, B, C, D) indicated, PCR analysis of tail DNA identified the configuration of the Igλ locus before and after Cre deletion. Oligonucleotides (1-6; see below) are indicated by arrows and resulting PCR bands are the product of used oligo combinations indicated by shading. Restriction sites used for the analysis are B, BamHI; H, HindIII; R, EcoRI; S, SacI; X, XhoI; Xb, XbaI;

FIG. 2 Shows flow cytometry analysis of a, bone marrow and b, splenic B-cell populations from normal (NM), $\kappa^{-/-}$, $\lambda 1^{-/-}\kappa^{-/-}$, $\lambda 1.3^{-/-}\kappa^{-/-}$, $\lambda 1.3.2^{-/-}\kappa^{-/-}$ and $\lambda 1-2\,\Delta^{-/-}\kappa^{-/-}$ mice. The profiles are representative for results obtained for at least 5 mice per group and show staining of gated bone marrow lymphocytes with PE-conjugated c-kit, biotin-conjugated anti-mouse CD43, biotin-conjugated anti-mouse CD25 or biotin-conjugated anti-IgM in combination with PE- or APC-conjugated anti-B220. Spleen cells were stained with biotin-conjugated anti-IgM, FITC-conjugated anti-IgD, biotin- or FITC-conjugated anti-λ and/or PE-conjugated anti-κ and APC-conjugated anti-B220 for setting the B-lymphocyte gate;

EXPERIMENTAL

Figure 2A:
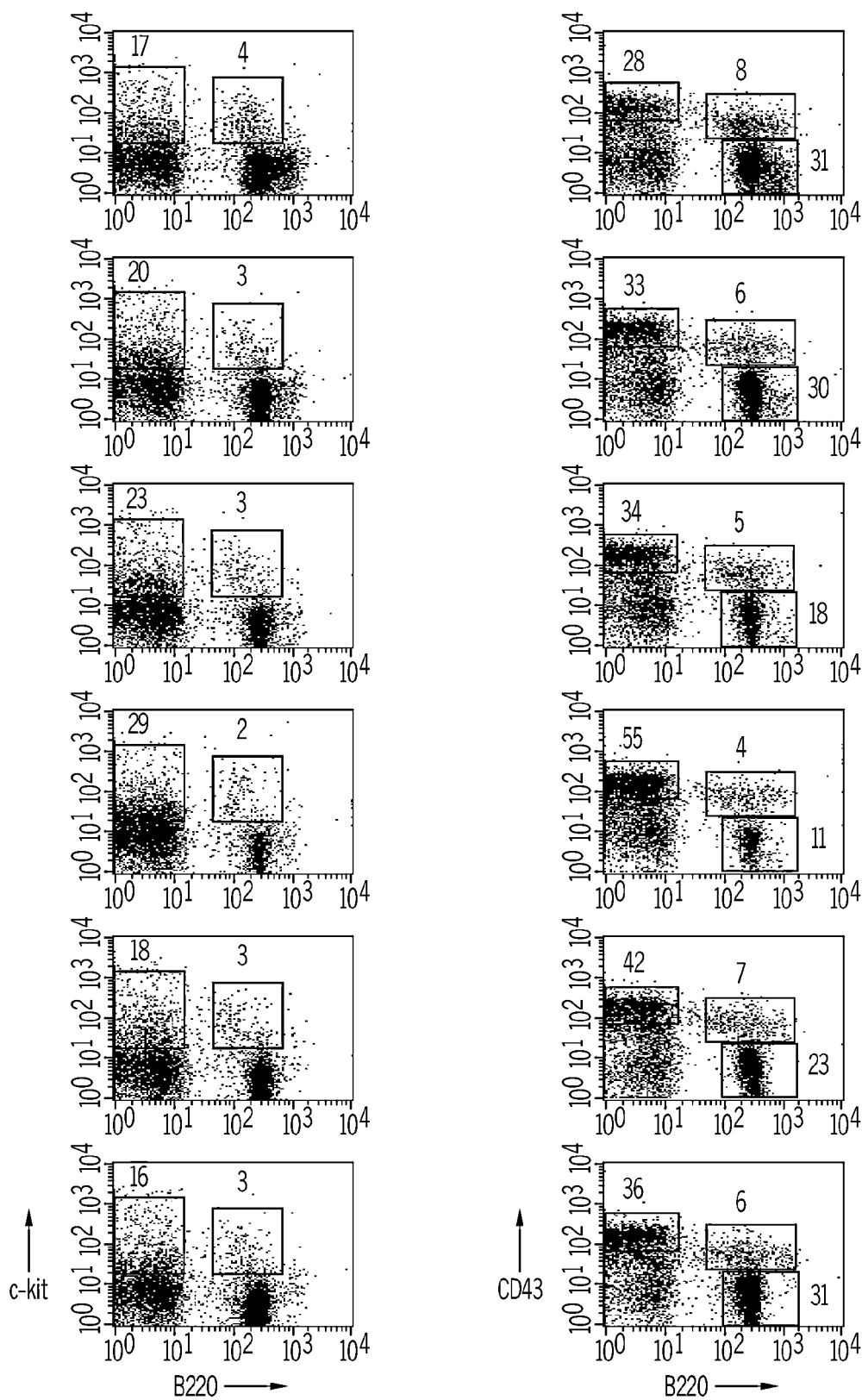

Here we show that mice with silenced L chain loci are immunodeficient. They do not produce B-1 or B-2 cells in the periphery and B-cell development is compromised at the immature B-cell stage with a complete block at the stage of differentiation when L chain rearrangement should have been completed.

To analyse the importance of light (L) chain expression for antibody development mutant mice with targeted deletion of the Igλ locus were generated and crossed with mice carrying a non-functional Igκ locus. Successive silencing, of Cλ genes in a $\kappa^{-/-}$ background showed a reduction in mature B-cell levels and animals with silenced L chain genes, i.e. $\lambda^{-/-}\kappa^{-/-}$ mice, do not express Ig polypeptides. Their spleens are devoid of B-cells and neither peritoneal B-1 nor B-2 cells are present whilst T-cell numbers remain normal. Bone marrow pro and pre B-cells are only slightly reduced and levels of CD25$^+$ large and small pre B-II cells are largely retained. In $\lambda^{-/-}\kappa^{-/-}$ mice B-cell development appears to be essentially uncompromised up to the immature stage. However, a complete block is apparent when L chain rearrangement, resulting in surface IgM expression, should be completed. The lack of L chain prevents BCR association and L chain function cannot be substituted (e.g. by surrogate light chain). Is was unexpected that the lack of L chain had no profound effect on precursor cell development, such as accumulation of pre B-II cells at the pre B- to immature B-cell transition stage.

Materials and Methods

Targeting Constructs.

A phage λ library derived from ES cell DNA, a kind gift from A. Smith and T. Rabbitts (Laboratory of Molecular Biology, MRC, Cambridge, UK), was hybridised with a Vλ and Cλ probe (clone #505 kindly provided by M. Neuberger, MRC, UK) which identified several clones containing Vλ and, separately, Cλ genes. Part of the C2-C4 and C3-C1 regions were subcloned in pUC19 to assemble the constructs and to obtain gene probes. This allowed blunt end insertion of loxP from pGEM-30 (Gu, H. et al., 1993, Cell 73: 1155-1164) in the HindIII site 3' of J3, loxP insertion in $^{tk}$Neo (Stratagene, La Jolla, Calif.) and blunt end insertion of $^{tk}$Neo-loxP into Cλ1, and loxP-$^{tk}$Neo, derived from pGH-1 (pGEM-30 and pGH-1 were a kind gift from H. Gu, Institute for Genetics, University of Cologne, Germany), into Cλ2 (see FIG. 1a). The ~14 kb C3-C1 targeting construct was obtained by XhoI and HindIII digest and the ~13 kb C2-C4 targeting construct was obtained by XhoI excision in the internal and polylinker site. Restriction sites for integration of $^{tk}$Neo (SacI and BamHI) or loxP (HindIII) in the targeting constructs were not maintained.

Analysis of Homologous Integration.

Methods used for electroporation of targeting constructs and ES cell selection have been described (Zou, X. et al., 1995, supra). The C3-C1 construct was integrated in HM-1 (Selfridge, J. et al., 1992, Somat. Cell. Mol. Genet. 18: 325-336) and C2-C4 was integrated in λES3.1Δ-5 ES cells. Targeting of C3-C1 was identified with a 0.4 kb HindIII fragment (probe A, all probes are marked in FIG. 1a) and SacI digest of ES cell DNA, and verified with a 2 kb XbaI-HindIII fragment (probe B) and SacI, HindIII and BamHI digests which also allowed identification of C3-C1 Cre-loxP deletion. Homologous integration in C2-C4 was identified with a 0.7 kb HindIII-XbaI fragment (probe C, the XbaI site is immediately 5' of SacI) and a 1.2 kb HindIII-BamHI fragment (probe D), and HindIII and BamHI digests of ES cell DNA. To obtain deletion of the λ locus the Cre plasmid pBS185 (GIBCO, #10347-011) was transiently integrated by electroporation (Zou, X. et al., 1995. supra). Clones were tested by PCR using the following oligonucleotides (arrow 1-6 in FIG. 1a):

```
C1rev
                                      (SEQ ID NO: 1)
5'-GCCTTTCCCATGCTCTTGCTGTCAGGG-3'  (<1);

C1for
                                      (SEQ ID NO: 2)
5'-CCAAGTCTTCGCCATCAGTCACCC-3'  (2>);

3'J3for
                                      (SEQ ID NO: 3)
5'-CCCAGGTGCTTGCCCCACAGGTTTAGG-3'  (3>);

5'C2for
                                      (SEQ ID NO: 4)
5'-GGAGATCAGGAATGAGGGACAAAC-3'  (4>);

3' $^{tk}$Neorev
                                      (SEQ ID NO: 5)
5'-CTCGACGGATCCGTCGAGGAATTCC-3'  (<5 neo);
and $^{tk}$Neofor
                                      (SEQ ID NO: 6)
5'-ATGGCCGATCCCATATTGGCTGCAGGG-3'  (neo 6>).
```

Oligos 1-2 and separately, 4-5 identified construct integration whilst the combination of oligos 1-3 and 1-4 identified partial or complete C gene deletion. PCR reactions were performed under the following conditions: two initial cycles of 45 sec at 97° C., 30 sec at 60° C. and 60 sec at 72° C. followed by 30 cycles with 30 sec at 94° C., 30 sec at 60° C. and 60 sec at 72° C., and 10 min at 72° C. to complete the reaction.

Derivation of Mice.

Chimeric mice and germline transmission was obtained as described (Hogan, B. et al., 1994a, In: Manipulating the mouse embryo, a laboratory manual, Cold Spring Harbor Laboratory Press, Cold Spring Harbor, p 253-289. λ1.3 mice, in a 129/Ola×Balb/c background, were mated with 129/Ola mice for 5 generations and crossed with Cre mice and each other to obtain homozygous λ1.3$^{-/-}$ mice. For the derivation of ES cells, blastocysts were collected and cultured on mitomycin-C treated feeder cells (Hogan, B. et al., 1994b, In: Manipulating the mouse embryo, a laboratory manual, Cold Spring Harbor Laboratory Press, Cold Spring Harbor, p 217-251). Several ES cell lines were obtained and λES3.1Δ-5, a female line, was used for integration of the C2-C4 targeting construct.

For the derivation of transgenic mice expressing Cre-protein ubiquitously, the Cre plasmid pBS185 was linearised with ScaI and purified using a DNA purification kit (Qiagen #28304). DNA was microinjected into the male pronucleus of F1 embryos (CBA×C57B1/6) according to standard methods (Hogan, B. et al., 1994b, supra) and several founders were produced, two of which showed a high gene/locus deletion rate when crossed with loxP mice.

Flow Cytometry Analysis.

For the analysis of B cell populations by flow cytometry cells from the different tissues were prepared and stained with various combinations of differently labelled antibodies against cell surface markers (see FIG. 2): these were for bone marrow cells PE-conjugated anti-mouse c-kit (CD117) (09995B; PharMingen), Phycoerythrin (PE)- or allophycocyanin (APC)-conjugated anti-mouse CD45R (B220) (01125A, 01129A; PharMingen, San Diego, Calif.), Biotin-conjugated anti-mouse CD25 (01092A; PharMingen), FITC-conjugated monoclonal rat anti-mouse IgM (μ chain specific, 04-6811; Zymed) and/or Biotin-conjugated anti-mouse CD43 (01602D; PharMingen); for spleen cells PE- or APC-conjugated anti-mouse CD45R (B220) (01125A, 01129A; PharMingen), Biotin-conjugated anti-mouse IgM (μ chain specific, 02082D; PharMingen), FITC-conjugated anti-mouse IgD (02214D); PharMingen), Biotin or FITC conjugated anti-mouse Igλ (02172D, 02174D; PharMingen) and/or PE-conjugated anti-mouse Igκ (559940, PharMingen); and for peritoneal cells PE-conjugated anti-mouse CD5 (Ly-1) (01035A; PharMingen) and APC-conjugated anti-mouse CD45R (B220) (01125A, 01129A; PharMingen).

For cytoplasmic staining bone marrow B-cells is were pre-treated using a fix and perm cell permeabilization kit (GSA-004, Caltag) and they stained with FITC-conjugated monoclonal rat anti-mouse IgM (μ chain specific, 04-6811; Zymed), PE-conjugated anti-mouse CD45R (B220) (01125A, 01129A; PharMingen) and Biotin-conjugated anti-mouse CD25 (01092A; PharMingen) according to the manufacturer's protocol. Binding of biotinylated antibody was developed with streptavidin-Quantum Red (S2899; Sigma) or strepavidin-Tri-color (SA1006, Caltag, Burlingame).

Protein Analysis.

Serum antibodies were identified by ELISA as described (Zou, X. et al., 1995, supra). For separation on acrylamide gels digitonin lysates of one marrow cells (Bell, S. E. et al., 1994, EMBO J. 13(4): 816-26) and, separately, serum was incubated for 1 h at 4° C. with anti-mouse IgM (μ chain specific, The Binding Site, Birmingham, UK) coupled to CNBr-activated Sepharose 4B (Pharmacia LKB, Uppsala, Sweden) as described (March, S. C. et al., 1974, Anal. Biochem. 60; 149-152). Samples were fractionated on 4-15% precast gels (161-1104, Bio-Rad, Hemel Hempstead, UK) and, after transfer to nitrocellulose membranes, incubated with biotinylated anti-mouse μ (B-9265, Sigma) for 1 h at RT and then placed in streptavidin biotinylated horseradish peroxidase (HRP) solution (RPN 1051, Amersham) for 30 minutes on a rocker. Bands were visualised with SuperSignal West Pico chemiluminescent substrate (34080, Pierce, Ill.).

Results

Silencing of the Mouse μ L Chain Locus.

To investigate B-cell development without L chain we produced mice with a deleted Igλ locus. The $\lambda^{-/-}$ mice were crossed with animals carrying a non-functional Igκ locus, $\kappa^{-/-}$ mice, also obtained by gene targeting (Zou, X. et al., 1995, supra). The mouse λ L chain locus contains 3 V (variable) region genes, 4 J (joining) segments and 4 C (constant) region genes which can independently rearrange and express 3 different λ L chains. C4 has not found to be expressed. Silencing of the locus was carried out in 4 successive steps by introduction of 3 loxP sequences and targeting of C1 and C2 (FIG. 1a). Introduction of the C3-C1 targeting construct silenced C1 and germline transmission mice were produced which, upon mating with ubiquitous Cre expressers, had C3-C1 deleted on both alleles. Such mice, bred into the 129/Ola background, were used for the derivation of embryonic stem (ES) cells which allowed homologous integration and silencing of C2. Germline transmission mice were obtained and bred with the Cre expressers and each other which resulted in homozygous animals with a C2 to C1 deletion of ~120 kb. Analysis of ES cells and mice by Southern blot and PCR, with representative examples shown in FIG. 1b, identified homologous integration and locus deletion and resulted in separate animals with the following genes silenced: a) $\lambda C1^{-/-}$ (mouse 130=ES1.3), b) $\lambda C1^{-/-}$ and $\lambda C3^{-/-}$ (mouse 1.3=ES1.3Δ), c) $\lambda C1^{-/-}$, $\lambda C2^{-/-}$ and $\lambda C3^{-/-}$ (mouse 50=ES2.4) and c) deletion of $\lambda C1^{-/-}$, $\lambda C2^{-/-}$, $\lambda C3^{-/-}$ and $\lambda C4^{-/-}$ (mouse 1.3-2.4Δ). These mouse strains were crossed into the $\kappa^{-/-}$ background and termed according to their silenced or deleted (Δ) C genes: $\lambda 1^{-/-}\kappa^{-/-}$, $\lambda 1.3^{-/-}\kappa^{-/-}$, $\lambda 1.3.2^{-/-}\kappa^{-/-}$ and $\lambda 1-2\Delta^{-/-}\kappa^{-/-}$. Deletion of the λ locus was verified by sequencing of the 686 bp PCR fragment shown in FIG. 1b which contained the 3' J2 and 3' C1 region separated by loxP.

B-Cell Reduction Upon Cλ Gene Removal.

Figure 2A:
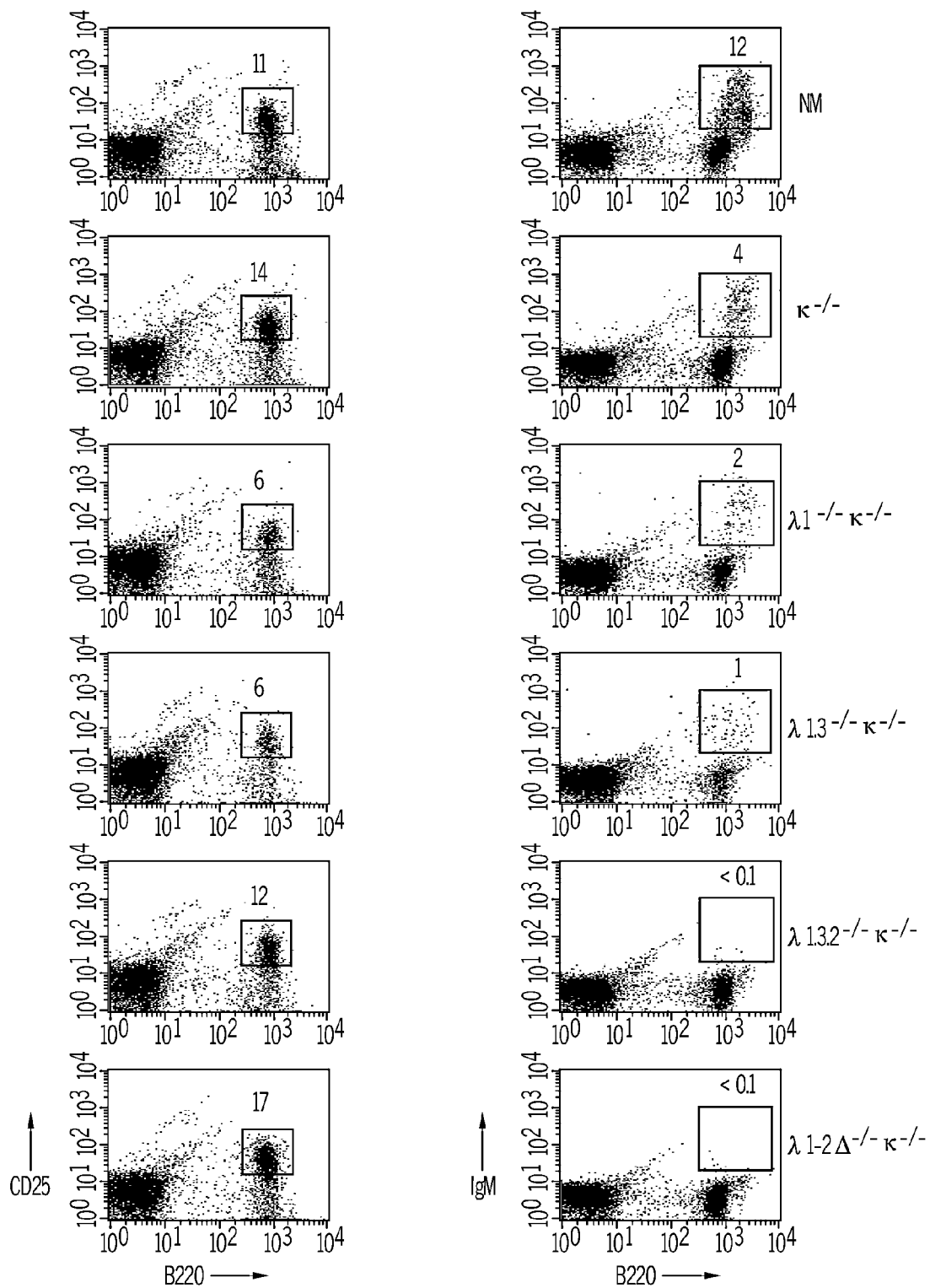
Figure 2B:
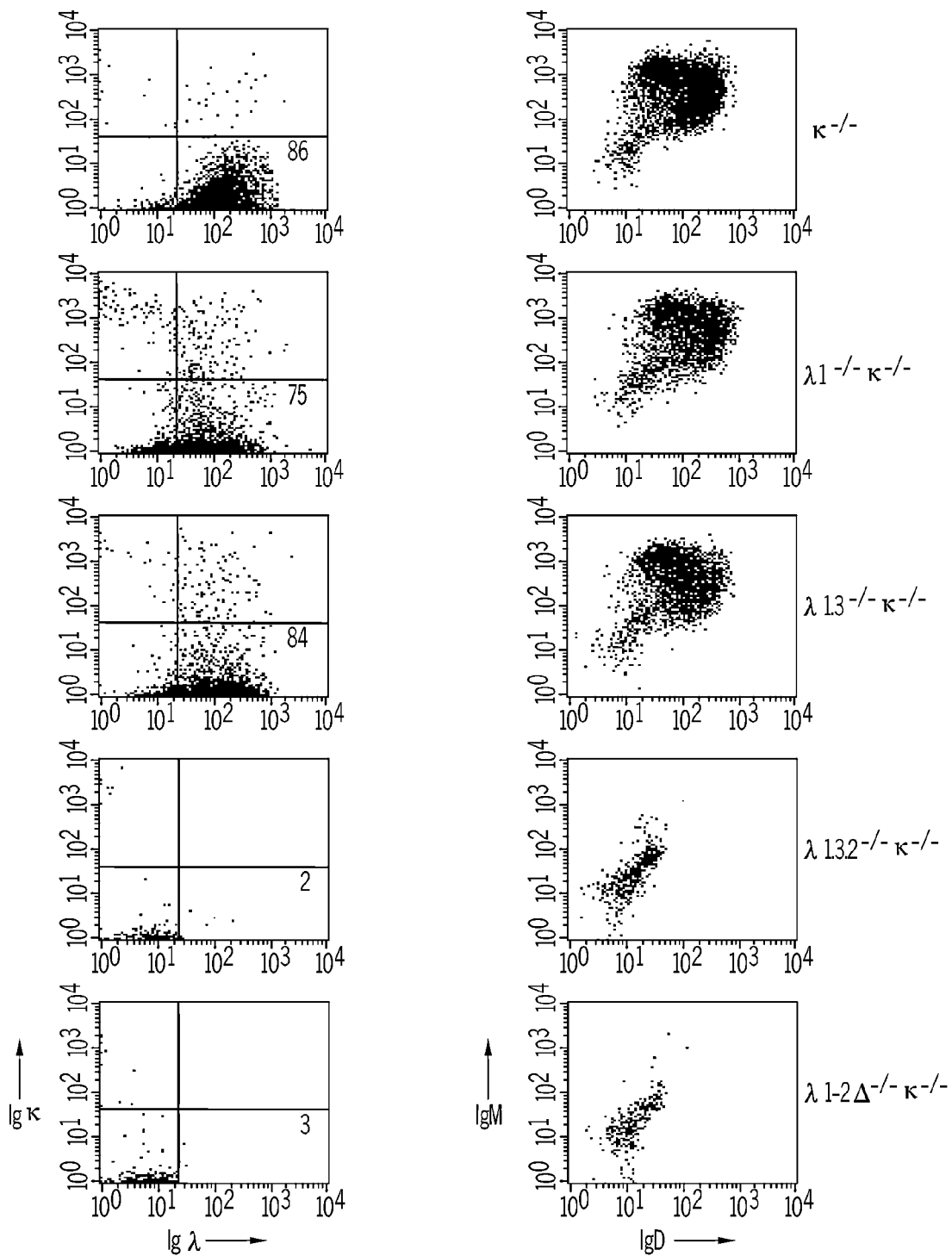

Mice with individually silenced Cλ genes in the $\kappa^{-/-}$ background showed significantly reduced numbers of mature IgM$^+$ B-cells compared to normal mice kept in the same pathogen-free conditions (Table 1). Serum antibodies in $\lambda 1^{-/-}\kappa^{-/-}$ and $\lambda 1.3^{-/-}\kappa^{-/-}$ were also reduced but comparable to those in $\kappa^{-/-}$ mice (Zou, X. et al., 1995, supra). Unexpectedly $\lambda 1.3.2^{-/-}\kappa^{-/-}$ and $\lambda 1-2\Delta^{-/-}\kappa^{-/-}$ mice derived from heterozygous females or foster mothers had significant antibody titers in serum still detectable by ELISA 6 weeks after weening. However, serum analyses from such mice older than 3 months showed that no antibodies remain (data not shown). The lack of serum Ig in $\lambda 1.3.2^{-/-}\kappa^{-/-}$ mice confirms that Cλ4 must be a pseudogene and that the remaining Vλ genes cannot be expressed using an as yet unknown C gene. The reduction of B-cell levels in bone marrow and spleen at each successive silencing step is shown in FIG. 2 and Table 1. In the bone marrow pro and pre B-cell development appears to be little affected by the loss of L chain expression and the levels of c-kit$^+$, CD43$^+$ and CD25$^+$ B-cells are quite similar in the KO strains and compared to normal mice (FIG. 2a). However, at the stage when L chain rearrangement should have been completed normal development is blocked and immature B-cells fail to express surface IgM. Interestingly, a reduction in the number of cells expressing surface IgM is clearly visible and, compared to the 12% of IgM$^+$ B220$^+$ lymphocytes in normal mouse bone marrow, 4% are found in $\kappa^{-/-}$ mice, 2% in $\lambda 1^{-/-}\kappa^{-/-}$, 1% in $\lambda 1.3^{-/-}\kappa^{-/-}$ and essentially none in $\lambda 1.3.2^{-/-}\kappa^{-/-}$ and $\lambda 1-2\Delta^{-/-}\kappa^{-/-}$ mice. In the spleen the levels of Ig$^+$ B-cells in $\lambda 1^{-/-}\kappa^{-/-}$ and $\lambda 1.3^{-/-}\kappa^{-/-}$ mice are similar to those in $\kappa^{-/-}$ mice whilst in $\lambda 1.3.2^{-/-}\kappa^{-/-}$ and $\lambda 1-2\Delta^{-/-}\kappa^{-/-}$ mice only background staining remains (FIG. 2b).

Figure 3A:
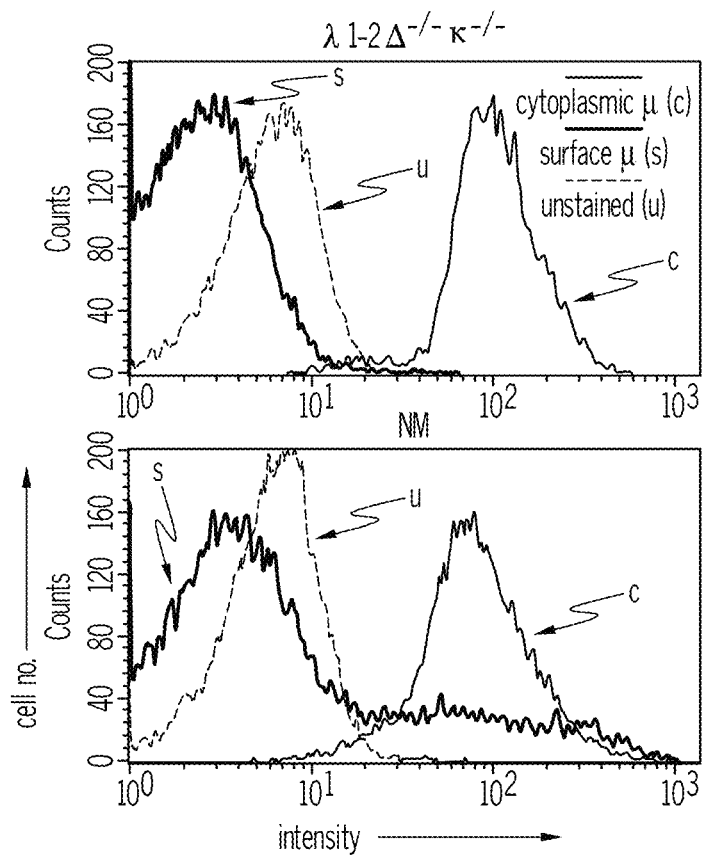
FIG. 3 Shows cytoplasmic and surface staining of CD25$^+$ bone marrow B-cells from $\lambda 1-2\Delta^{-/-}\kappa^{-/-}$ and normal (NM) mice. a, cytoplasmic and separately, surface staining with FITC-coupled anti-μ. b, separation of B-cells according to their size.
Figure 3B:
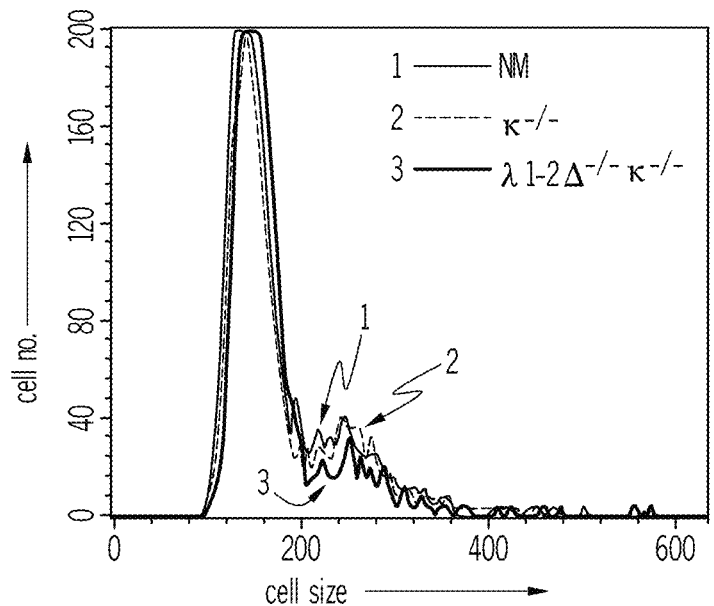
Figure 4:
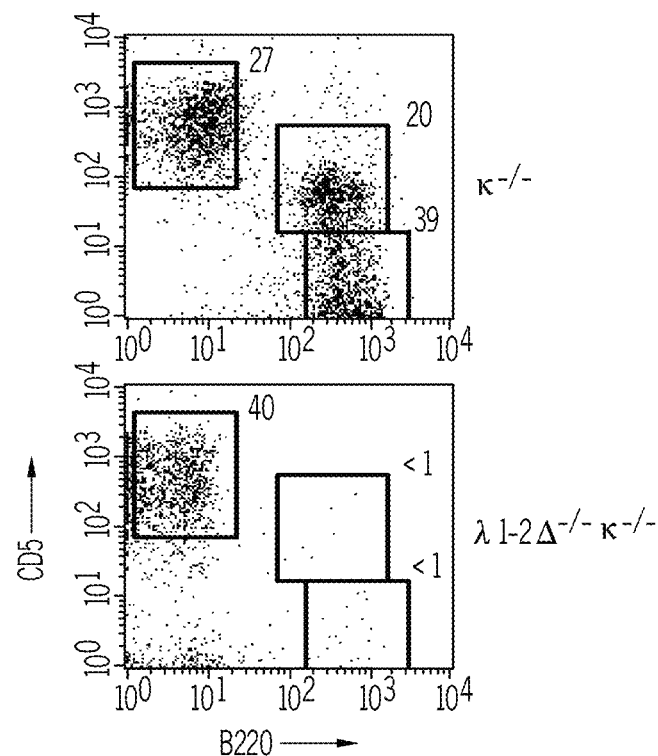
FIG. 4 Shows flow cytometry analysis of B- and T-cells in the peritoneum of $\kappa^{-/-}$ and $\lambda 1-2\Delta^{-/-}\kappa^{-/-}$ mice. Cells were stained with PE-conjugated anti-CD5 and APC-conjugated anti-B220.
Figure 5:
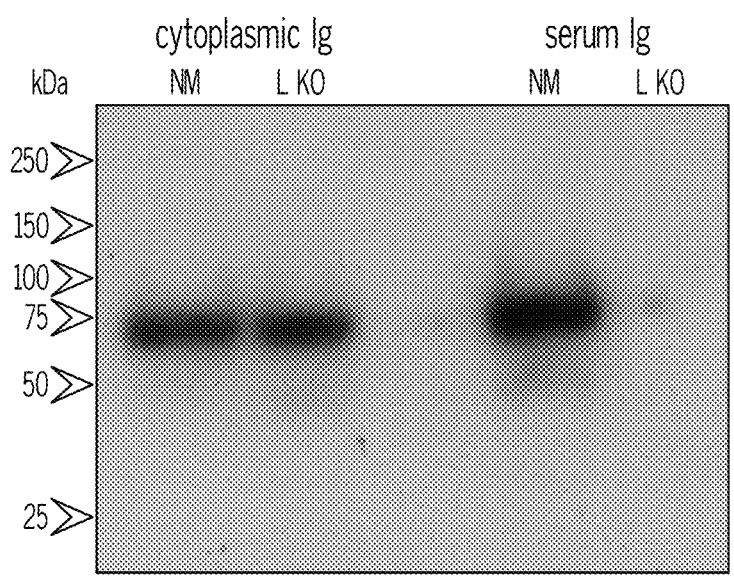
FIG. 5 Shows gel separation of cytoplasmic and serum antibodies from $\lambda 1-2\Delta^{-/-}\kappa^{-/-}$ (L KO) and normal (NM) mice captured with anti-μ.

To evaluate if B220$^+$ B-cells in the bone marrow do accumulate μ H chain in the cytoplasm and if these cells migrate to secondary lymphoid organs we stained for cytoplasmic IgM. As shown in FIG. 3a CD25$^+$ bone marrow B-cells from $\lambda 1-2\Delta^{-/-}\kappa^{-/-}$ mice do indeed stain for cytoplasmic μ H chain but show no staining for surface IgM. Indeed the levels of CD25$^+$ B-cells and their size distribution is very similar in normal and L KO mice (FIG. 3b). However, migration of these cells to, for example, the peritoneum is not taking place and FIG. 4 shows that essentially no B-cells exist in secondary lymphoid organs. We wondered if the identified μ H chain in the cytoplasm of B-cells from $\lambda 1-2\Delta^{-/-}\kappa^{-/-}$ mice is of the same size or molecular weight as conventional μ H chain. Cell lysis using digitonin and capturing bound or unbound μ H chain, analysed on polyacryamide gels (FIG. 5), showed no size difference of the μ H chain produced in the cytoplasm of normal or L chain silenced mice. However, as also shown in FIG. 5 serum Ig is not produced by these mice. This re-emphasises that B-cell development and μ H chain expression up to the stage when L chains are expressed appears to be largely unaffected in L chain KO mice. Furthermore, the lack of L chain prevents the release of μ H chain from the cell which prevents Ig secretion.

Block in Development at the Immature B-Cell Stage.

Silencing of the λ L chain genes in a $\kappa^{-/-}$ background showed that no surface or secreted Ig is produced and that the resulting block in B-cell development is established at the pre B-II to immature transition phase. At this stage CD25 expression is revoked, the pre BCR is replaced by the BCR, surrogate L chain is no longer expressed and κ or λ L chain rearrangement is completed with successful expression that allows μ H chain association. After several divisions large CD25$^+$ pre B-II cells differentiate into small CD25$^+$ resting pre B-II cells which are in the process of rearranging their L chain genes. As can be seen in FIG. 2a the number of CD25$^+$ B220$^+$ cells at the stage immediately before the developmental block is by and large very similar. As successful L chain rearrangement is prevented or impaired in the mutant mice we wondered if this block in development alters the ratio of large and small CD25$^+$ cells. In FIG. 3b the number of CD25$^+$ gated hone marrow cells from age-matched normal, $\kappa^{-/-}$ and $\lambda 1-2\Delta^{-/-}\kappa^{-/-}$ mice is plotted against cell size. The comparison shows slight variations as expected but no major differences in the large and small pre B-II cell populations. This concludes that the failure to express L chain initiates a complete block in development at the immature B-cell stage when surface IgM should be expressed. In addition no immature B-cells accumulate before the event.

This block in development with no apparent recovery impedes surface IgM expression and subsequent cell migration. As shown in Table 1 the number of spleen cells in $\lambda 1.3.2^{-/-}\kappa^{-/-}$ and $\lambda 1-2\Delta^{-/-}\kappa^{-/-}$ mice is significantly reduced. A complete lack of mature B-cells is also found in the peritoneal cavity with no B220$^+$ and B220$^+$CD5$^+$ cells (FIG. 4). This lack of B-1 and B-2 cells appears to have no effect on T-cell levels which are maintained.

Discussion

Our experiments show that B-cell development is aborted in L chain deletion mice at the pre B-II to immature B-cell transition stage when surface receptor expression should have been accomplished. This complete block in development prevents B-cell maturation and the mouse is immunodeficient regarding antibody expressing B-cells. The surrogate L chain encoded by VpreB and λ5 does not sustain B-cell development and with the failure to express L chain polypeptides B-cell differentiation ceases exactly at the stage when L chain rearrangement should have been completed. This re-emphasises the importance of L chain for immune development and that, at least in the mouse, there is no gene or rescue event that can compensate L chain deficiency.

B-cell development in the mouse has been extensively studied by gene targeting and in one of the early experiments a μ transmembrane exon was rendered non-functional which prevented surface IgM expression. This μMT KO caused a block in development, leading to the accumulation of pre B-I and the disappearance of pre B-II cells. With the lack of surface IgM expression no proliferation or differentiation into immature or mature B-cells was obtained, however, DNA rearrangement was maintained. Indeed the μMT mice do rearrange H and L chain genes whilst H chain KO mice without J segments maintain L chain rearrangement. This is in agreement with the results of our $\lambda^{-/-}\kappa^{-/-}$ mice which show H chain rearrangement and cytoplasmic Igμ expression which reiterates that H and L chain rearrangement and expression are independent events. The critical importance of the BCR in signalling and normal progression of development through the different B-cell maturation stages was further analysed by gene targeting of individual BCR components. The results showed that silencing of some genes, such as the Igκ L chain locus, had a moderate effect on B-cell development and is well tolerated whilst the function of other genes, such as Cμ or Igβ, is essential and blocks any progress in development. The block in B-cell development was frequently accompanied by the accumulation of cells prior to the stage of differentiation when the silenced gene should be active. Surprisingly this is not seen at any pro or pre B-cell stage in the $\lambda^{-/-}\kappa^{-/-}$ mice and the numbers of CD25$^+$ large and small B-cells immediately prior to the block in development are similar to those found in a normal mouse. A reason for this may be that the cells entering the pre B-II stage and those being apoptosed, perhaps half of the CD25$^+$ cells generated in the bone marrow die without maturing into IgM$^+$ B-cells, allow to maintain fairly constant cell levels.

The importance of L chain expression has been studied in RAG-1 and RAG-2 KO mice where B-cell development is arrested at the B220$^+$CD43$^+$ pro B-cell stage. Upon introduction of a rearranged H chain Igμ was expressed in the cytoplasm which is in agreement with the observation that L chain facilitates dissociation of H chain binding protein and transport to the cell surface. However, to direct the development of a B-lineage cell population in RAG$^{-/-}$ mice both rearranged H and L chain genes had to be introduced. In the bone marrow of RAG-1$^{-/-}$λ5$^{-/-}$ mice carrying a rearranged H chain transition from pro B- to pre B-cell and surface IgM expression was only seen when either λ5 or a rearranged L chain was introduced. Nussenzweig and colleagues argued that when neither λ5 nor conventional L chain are expressed B cell development cannot proceed past the pro-B-cell stage. This is not seen in our mice with silenced λ and κ light chain locus where B-cell development allows heavy chain expression and developmental progress to the pre B-II cell stage.

This application claims the benefit of priority to GB 0115256.0 which was filed on Jun. 21, 2001.

TABLE 1

Cell numbers in spleen and bone marrow of normal, $\kappa^{-/-}$ and C λ deletion mice.

| Organ | NM | $\kappa^{-/-}$ | $\lambda 1^{-/-}\kappa^{-/-}$ | $\lambda 1.3^{-/-}\kappa^{-/-}$ | $\lambda 1.3.2^{-/-}\kappa^{-/-}$ | $\lambda 1$-$2\Delta^{-/-}\kappa^{-/-}$ |
|---|---|---|---|---|---|---|
| Bone Marrow | | | | | | |
| total cell no. × 10$^6$* | 18 | 14 | 9 | 6 | 2 | 1 |
| c-kit$^+$, B220$^+$ pro B-cells | 0.52 | 0.24 | 0.14 | 0.08 | 0.04 | 0.02 |
| B220$^+$, CD43$^+$ pro/pre B-cells | 0.95 | 0.51 | 0.29 | 0.16 | 0.08 | 0.04 |
| B220$^+$, CD25$^+$ immat. B-cells | 1.32 | 1.28 | 0.38 | 0.21 | 0.14 | 0.10 |
| B220$^+$, IgM$^+$ immat./mat. B-cells | 1.34 | 0.33 | 0.10 | 0.05 | 0.01 | 0.10 |
| B220$^+$ B-cells | 3.89 | 2.81 | 1.00 | 0.48 | 0.27 | 0.18 |
| IgM$^+$ B-cells | | | | | | |
| Spleen | | | | | | |
| total cell no. × 10$^6$ | 38 | 42 | 28 | 32 | 31 | 24 |
| B220$^+$ | 10.40 | 7.42 | 3.62 | 4.31 | 0.67 | 0.39 |
| IgM$^+$ | 0.69 | 6.60 | 3.10 | 3.74 | 0.03 | 0.02 |
| IgD$^+$ | 7.81 | 3.10 | 1.18 | 1.51 | <0.01 | <0.01 |
| IgL$^+$ | | | | | | |

Cells were stained with relevant antibodies for the listed features (see Materials and Methods) and analysed by
Total cell numbers were determined by Trypan blue staining.
*Cells were from one femur.

The invention claimed is:

1. A knock-out mouse having its mouse immunoglobulin lambda light chain locus deleted in part or completely through targeted integration and gene deletion or through gene deletion of segments encoding for the lambda light chain locus, wherein the complete or partial deletion of the mouse immunoglobulin lambda light chain locus consists of (1) a deletion of or targeted integration in lambda light chain gene C2 and a deletion of lambda light chain genes C3-C1; or (2) a deletion of lambda light chain genes C2, C4, C3 and C1.

2. A knock-out according to claim 1, wherein the complete or partial deletion of the mouse immunoglobulin lambda light chain locus consists of a deletion of the lambda light chain genes C2, C4, C3 and C1.

3. A knock-out mouse according to claim 1, wherein mouse has its lambda light chain locus deleted in part or completely through targeted integration using loxP constructs as targeting constructs.

4. A knock-out mouse according to claim 2, wherein the lambda light chain genes C2, C4, C3 and C1 are deleted through targeted integration using loxP constructs as targeting constructs.

5. The knock-out mouse according to claim 1, wherein the mouse immunoglobulin κ light chain locus is functionally silenced by targeted integration of a selectable marker gene in Cκ or targeted deletion of Cκ or Jκ.

6. The knock-out mouse according to claim 1, wherein the mouse immunoglobulin heavy chain locus is functionally silenced by targeted integration of a selectable marker gene in the μ membrane exons or targeted deletion of the JH gene segments.

7. The knock-out mouse according to claim 1, wherein the knock-out mouse comprises one or more heavy and/or a light chain immunoglobulin genes or loci from a human.

8. The knock-out mouse according to claim 5, wherein the mouse immunoglobulin heavy chain locus is functionally silenced by targeted integration of a selectable marker gene in the μ membrane exons or targeted deletion of the JH gene segments.

* * * * *

UNITED STATES PATENT AND TRADEMARK OFFICE
CERTIFICATE OF CORRECTION

PATENT NO. : 9,439,405 B2  
APPLICATION NO. : 13/654007  
DATED : September 13, 2016  
INVENTOR(S) : Marianne Brüggemann et al.

Page 1 of 1

It is certified that error appears in the above-identified patent and that said Letters Patent is hereby corrected as shown below:

In the Claims:

Claim 2, starting at column 13, Line 12, should read:

2. A knock-out mouse according to claim 1, wherein the complete or partial deletion of the mouse immunoglobulin lambda light chain locus consists of a deletion of the lambda light chain genes C2, C4, C3 and C1.

Signed and Sealed this  
Thirteenth Day of December, 2016

Michelle K. Lee  
*Director of the United States Patent and Trademark Office*

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence

```
<220> FEATURE:
<223> OTHER INFORMATION: Description of Artificial Sequence: Synthetic
      polynucleotide sequence

<400> SEQUENCE: 1
gcctttccca tgctcttgct gtcaggg                                              27

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 2
ccaagtcttc gccatcagtc accc                                                 24

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 3
cccaggtgct tgccccacag gtttagg                                              27

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 4
ggagatcagg aatgagggac aaac                                                 24

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 5
ctcgacggat ccgtcgagga attcc                                                25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 6
atggccgatc ccatattggc tgcaggg                                              27
```